(12) United States Patent
Neff

(10) Patent No.: US 9,218,455 B2
(45) Date of Patent: Dec. 22, 2015

(54) DYNAMIC PAIRING OF DEVICES WITH A MEDICAL APPLICATION

(71) Applicant: Cerner Innovation, Inc., Kansas City, KS (US)

(72) Inventor: Robert A. Neff, Villanova, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 14/032,435

(22) Filed: Sep. 20, 2013

(65) Prior Publication Data

US 2014/0067426 A1 Mar. 6, 2014

Related U.S. Application Data

(63) Continuation-in-part of application No. 13/349,614, filed on Jan. 13, 2012.

(60) Provisional application No. 61/548,787, filed on Oct. 19, 2011.

(51) Int. Cl.
*G06F 19/00* (2011.01)
*H04W 4/00* (2009.01)

(52) U.S. Cl.
CPC .......... *G06F 19/3406* (2013.01); *G06F 19/322* (2013.01); *H04W 4/008* (2013.01)

(58) Field of Classification Search
CPC .................................................. G06F 19/3406
USPC .................... 235/375, 462.46, 472.02; 705/2; 455/456.3
See application file for complete search history.

(56) References Cited

U.S. PATENT DOCUMENTS

| | | | |
|---|---|---|---|
| 5,696,365 A | 12/1997 | Ukai et al. | |
| 6,283,647 B1 | 9/2001 | Konishi et al. | |
| 7,278,579 B2 * | 10/2007 | Loffredo et al. | 235/462.46 |
| 7,703,682 B2 | 4/2010 | Kenney | |
| 7,708,198 B2 | 5/2010 | Gangi | |
| 7,712,658 B2 | 5/2010 | Gangi | |
| 7,967,190 B2 | 6/2011 | Hussey | |
| 2002/0132585 A1 | 9/2002 | Palermo et al. | |
| 2002/0161708 A1 | 10/2002 | Offer | |
| 2003/0144035 A1 | 7/2003 | Weinblatt et al. | |
| 2004/0172300 A1 | 9/2004 | Mihai et al. | |
| 2005/0101844 A1 | 5/2005 | Duckert et al. | |
| 2005/0277872 A1 | 12/2005 | Colby et al. | |
| 2006/0106648 A1 | 5/2006 | Esham et al. | |
| 2008/0011825 A1 | 1/2008 | Giordano et al. | |
| 2008/0017722 A1 | 1/2008 | Snyder et al. | |
| 2008/0028214 A1 * | 1/2008 | Tafoya et al. | 713/166 |
| 2008/0189170 A1 | 8/2008 | Ramachandra | |
| 2008/0198028 A1 | 8/2008 | Watanabe | |
| 2008/0261526 A1 | 10/2008 | Suresh | |
| 2009/0037515 A1 * | 2/2009 | Zapata et al. | 709/202 |
| 2009/0112072 A1 | 4/2009 | Banet et al. | |

(Continued)

*Primary Examiner* — Allyson Trail
(74) *Attorney, Agent, or Firm* — Shook, Hardy & Bacon, L.L.P.

(57) ABSTRACT

Mobile or embedded devices are dynamically paired with medical applications. By displaying identifying information associated with the medical application and capturing the display with a sensing device, the identifying information may be used by a server to route sensed data from the sensing device to the medical application for the patient. Barcodes or other identifying information may be used. The mobile device may be a smart phone, allowing smart phones to be dynamically paired with the medical application as desired by the user.

20 Claims, 15 Drawing Sheets

(56) References Cited

U.S. PATENT DOCUMENTS

| | | |
|---|---|---|
| 2010/0001838 A1 | 1/2010 | Miodownik et al. |
| 2010/0012715 A1 | 1/2010 | Williams et al. |
| 2010/0038417 A1 | 2/2010 | Blankitny |
| 2010/0065634 A1 | 3/2010 | Nakamura |
| 2010/0169120 A1 | 7/2010 | Herbst et al. |
| 2010/0169121 A1 | 7/2010 | Herbst et al. |
| 2010/0219242 A1 | 9/2010 | Gangi |
| 2010/0230485 A1 | 9/2010 | Kenney |
| 2010/0271208 A1 | 10/2010 | Steinmetz et al. |
| 2011/0072263 A1* | 3/2011 | Bishop et al. ............ 713/168 |
| 2011/0081860 A1 | 4/2011 | Brown et al. |
| 2011/0101115 A1 | 5/2011 | Rampersad |
| 2011/0131061 A1* | 6/2011 | Shain ............ 705/3 |
| 2011/0210170 A1 | 9/2011 | Arguello |
| 2011/0297747 A1 | 12/2011 | Naumovsky |
| 2011/0302051 A1* | 12/2011 | Arbatli ............ 705/26.8 |
| 2011/0313870 A1 | 12/2011 | Eicher et al. |
| 2012/0029303 A1 | 2/2012 | Shaya |
| 2012/0041782 A1* | 2/2012 | Morris ............ 705/3 |
| 2012/0072536 A1 | 3/2012 | Xu et al. |
| 2012/0179908 A1 | 7/2012 | Duma |
| 2012/0205441 A1 | 8/2012 | Utech et al. |
| 2013/0013548 A1 | 1/2013 | Alexander et al. |
| 2013/0185092 A1 | 7/2013 | Dubbels et al. |
| 2014/0288947 A1 | 9/2014 | Simpson et al. |

\* cited by examiner

Figure 4

Application Data Tracking

| ULID | ULID Type | ULID Description |
|---|---|---|
| 900001 | Text Field | Patient Name Field on Screen Internet Explorer Session ID A91KM188X73 |
| 900002 | Overall Workflow (multi screen) | Workflow on Screen Internet Explorer Session ID A91KM188X73N |
| 900003 | Single Screen | Current Screen for User LNAMEFNAME00 |
| 900004 | Text Box | Text Box 1 on Screen for User LNAMEFNAME00 |
| 900005 | Radio Button Selection | Submit Button 1 on Screen for User LNAMEFNAME00 |
| 900006 | Dropdown Selection | Dropdown Box 2 on Internet Explorer Session ID MA91M47SNROX74VS7 |
| 900006 | Text Field | Drug Name Field on Screen for User LNAMEFNAME00 |
| 900007 | Task id | Task Id of specific task in a workflow process |
| 900008 | Workflow process id | Workflow process identifier |

Server Data Tracking

| Unique Location ID | Unique Location ID Type | Association Barcode | Barcode Wand ID | Application ID |
|---|---|---|---|---|
| 900001 | Text Field | 2000000001 | WAND1 | APL1 |
| 900002 | Overall Workflow (multi screen) | 2000000002 | WAND2 | APL1 |
| 900003 | Single Screen | 2000000003 | WAND3 | APL1 |
| 900004 | Text Box | 2000000004 | WAND4 | APL1 |
| 900005 | Radio Button Selection | 2000000005 | WAND5 | APL1 |
| 900006 | Dropdown Selection | 2000000006 | WAND6 | APL1 |
| 900006 | Text Field | 2000000007 | WAND7 | APL2 |
| 900007 | Task Id of specific task in a workflow process | 2000000008 | WAND7 | APL2 |
| 900008 | Workflow process | 2000000009 | WAND7 | APL2 |

503 — Unique Location ID
505 — Unique Location ID Type
507 — Association Barcode
509 — Barcode Wand ID
511 — Application ID

FIG. 16

DYNAMIC PAIRING OF DEVICES WITH A MEDICAL APPLICATION

This is a continuation-in-part of U.S. patent application Ser. No. 13/349,614, filed Jan. 13, 2012, which claims the benefit of priority under 35 U.S.C. §119(e) of U.S. Provisional Patent Application Ser. No. 61/548,787, filed Oct. 19, 2011, by R. A. Neff, the disclosures of which are incorporated herein.

FIELD

The present embodiments concern pairing of a mobile device with a sensor to a medical application. For example, a smart phone is linked to a medical record on a computer for entering information from the sensor into the database of the medical record. As another example, a bar code is associated with a particular bar code scanner and a data destination associated with a particular executable application so that data acquired using the particular bar code scanner is communicated to the data destination.

BACKGROUND

In known systems, a single barcode is typically directly associated with a barcode data receiving device to support an association between the bar code and the device in a computer system, for example. Barcode readers are used with a medical device or other non-PC systems that incorporate embedded software. In industry and healthcare settings, barcode readers are used to capture information from a bar code label and insert it into a software system. This is usually done by using a barcode reader which is connected to a computer system or device. In this case, the data is read from a paper printed barcode label and inserted into an appropriate data field in storage in a system to which the barcode reader is attached. For other sensors, a similar direct connection arrangement may be used.

In known systems, a barcode reader typically needs to be physically connected to the system receiving the barcode data. If a wireless barcode reader is deployed, the barcode reader is still required to be matched with a specific device and the device is required to support a driver or connection option for a barcode reader (Serial, USB, or keyboard). In known systems that use a Bluetooth wireless barcode reader, for example, a user needs to use the barcode to scan a particular PC with which to setup a Bluetooth connection. The barcode reader is then associated to that PC.

Other than barcodes, a user may desire to input an image into a medical record of a patient. The process for attaching an image to a document or other part of a workflow on a desktop requires that the image be loaded on the desktop as a file. Then, the image is selected from the file system on the desktop to be attached or inserted into the medical record. Smart phones are great for taking photos, but the photo must be saved, uploaded, and selected on a desktop to attach the photo to a document or desktop application. Due to HIPAA and other privacy regulations, this is a troublesome process due to the image file residing in multiple locations along the way. This is also a cumbersome process.

SUMMARY

A system enables wireless barcode readers to be used in a processing environment including different devices and different software applications by dynamic assignment of a barcode reader device to a software application using a barcode system server and "association" barcodes including both physical barcodes and dynamically created on-screen software generated barcodes. A bar code generation and processing system for medical and other use comprises at least one repository and a bar code processor. The at least one repository of information includes, identification data of multiple bar code scanners and also associates a bar code displayed in an image associated with an executable application and presented on a device with, the executable application and at least one of, (a) the device and (b) a data destination associated with the application. The bar code processor receives identification data of a bar code scanner and data representing the bar code displayed in the image and uses the information in associating the bar code with the data destination associated with the application and a particular bar code scanner of the multiple bar code scanners. The bar code processor communicates data acquired using the particular bar code scanner to the data destination in response to the association.

The same system or another system enables dynamic pairing of other mobile or embedded devices with a medical application (software application). By the medical application displaying identifying information associated with the medical application and capturing the display of such identifying information with the mobile or embedded device, the identifying information may be used by a server to route sensed data for a patient to the medical application. The mobile device may be a smart phone, allowing smart phones to be dynamically paired with the medical application as desired by the user.

In a first aspect, a method is provided for dynamic pairing of a mobile device with a medical application. The medical application is operated on a computer. The medical application includes patient information from a patient medical record of a patient. An association output image is displayed on a display of the computer. The association output image is linked to the computer. The association output image on the display is captured with the mobile device. An object associated with the patient is sensed with the mobile device. Sensed information from the sensor is routed to the computer using the captured association output image.

In a second aspect, a non-transitory computer readable storage medium has stored therein data representing instructions executable by a programmed processor for dynamic pairing of a device with a medical application. The storage medium includes instructions for linking an identifier to an instance of a medical application running on a remote computer; receiving sensor data and the identifier from the device, the identifier displayed by the remote computer and captured by the device from the display; associating, with the identifier, the sensor data with the instance of the medical application running on the remote computer; and outputting the sensor data to the instance of the medical application running on the remote computer.

In a third aspect, a system is provided for dynamic pairing of a device with a medical application. A display on a computer is configured to present an image associated with an executable electronic medical record application of the computer. A processor of the computer is configured to communicate identity information for the image with a remote server, to receive sensor data from the remote server, the sensor data and the image sensed by the device, and to insert the sensor data into a patient's electronic medical record of the executable electronic medical record application.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWING

FIG. 4 shows a lookup Table linking a unique location identifier, task identifier or process identifier (ULID) with unique location, task or process type of an associated executable application and with a description, according to invention principles.

FIG. 5 shows a Table linking a unique location identifier, task identifier or process identifier (ULID) with unique location, task or process type of an associated executable application, associated bar code, bar code scanner identifier and with an identifier of the executable application, according to invention principles.

FIG. 16 shows another example display image of the medical record application of FIG. 14, but with an added image from a dynamically linked sensor device.

DETAILED DESCRIPTION

Figure 1:
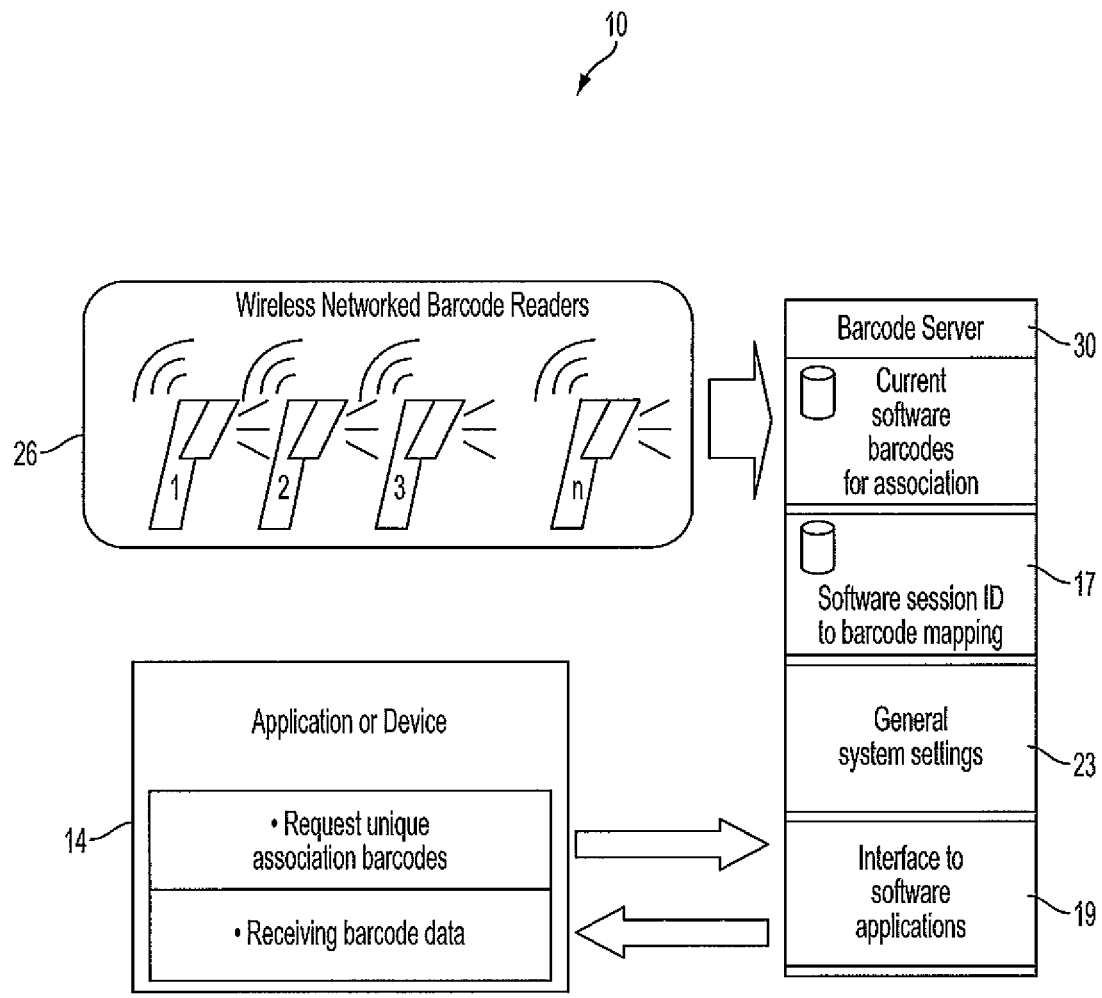
FIG. 1 shows a bar code generation and processing system for medical and other use, according to invention principles.

A system is provided to link a device with a medical application. The link is used to provide data from the device to the medical application. For example, a smart phone sends image data from a camera to the appropriate receiving system. A non-mobile computer application has an option to attach or include an image to the workflow (e.g., creating a document, uploading an image for analysis, entering a note on a patient record, etc.). When the workflow is ready to choose the image of the patient, either due to an action from the user or as an automated part of the workflow, a barcode, QRcode, or other linking image is shown on the screen. The user may then scan the linking image on the screen with their smart phone, which will then launch the camera application. After the image is acquired with the camera on the smart phone, the image is transferred wirelessly for use in the specific workflow on the desktop application. A server receives the image of the patient and the linking image or code and uses the linking information to route the image of the patient to the medical application.

Any smart phone, embedded device, or other sensor may be used with a medical records documentation system. Rather than requiring a physical link or direct communications between the computer with the medical application and the device running the application, the displayed identifying information from the computer is used to route the sensed data from the device to the application or computer. Existing desktop devices for entering medical records data can take advantage of inputting image data while not requiring any hardware updates (e.g., addition of webcams), physical links (e.g., cable connection), and/or drivers for establishing communications channels (e.g., Bluetooth) with the device.

Similarly, barcode readers may be linked with applications by dynamic assignment. Example embodiments of dynamic assignment of barcode readers to applications are discussed below. Other embodiments using smart phones or other devices are then discussed. The system described for barcode readers may be used with smart phones, embedded devices, or other devices.

Barcode Reader Embodiments

A system enables wireless barcode readers to be used throughout a software system and on different devices using different software applications by dynamic assignment of a barcode reader device to a software application and elements of the application as well as to associated tasks and processes. The system utilizes a barcode system server and "association" barcodes which might include both physical barcodes and dynamically created on-screen software generated barcodes.

The system enables multiple barcode readers to be deployed throughout an organization. The devices receiving the barcode data are not required to support barcode readers with particular types of driver or connection. This means existing devices may employ firmware modified according to invention principles to take advantage of the barcode system without requiring new hardware or hardware modifications. Also the system enables provision of a barcode reader association for a specific software application or image, not just an entire processing device or PC, for example. Specifically, the system advantageously enables association of a barcode reader with a specific software application, image, or text field allowing greater flexibility than associating the reader to a complete processing device.

FIG. 1 shows bar code generation and processing system 10 for medical and other use. System 10 includes one or more processing devices on network 21 (e.g., medical device, infusion pump, workstation, computer or portable devices such as notebooks, Personal Digital Assistants, phones) 12 that individually include a user interface enabling user interaction with a Graphical User Interface (GUI) and display 14 supporting GUI and executable application display image presentation. Processing device 12 executes Application 34 and includes communication processor 16 and the display 14. System 10 also includes bar code scanners 26 including scanners 41 and 42 in wired or wireless communication with server 30 via network 21 or another communication link. Bar code server (processor) 30 includes at least one repository 17, a general system settings function 23 and interface 19 to executable applications (e.g. Application 34).

At least one repository 17 includes identification data of multiple bar code scanners 26 and includes information associating a bar code displayed in an image with executable application 34 and with at least one of, (a) device 12 and (b) a data destination associated with Application 34. The image is associated with Application 34 and is presented on device 12. Bar code processor (server) 30, receives identification data of bar code scanner 41 and data representing the bar code displayed in the image and uses the information in associating the bar code with the data destination associated with application 34 and particular bar code scanner 41 of multiple bar code scanners 26. Bar code processor 30 communicates data acquired using the particular bar code scanner to the data destination in response to the association. Wireless barcode readers 26 operate over a standard wireless network in an enterprise such as a hospital. Processor 30 manages unique onscreen association barcodes and uses repository 17 in tracking mapping between currently associated barcode reader devices and active software sessions. Processor 30 enables addition of wireless barcode readers to the system and change of system configuration. Interface 19 provides an interface that operates over different types of network to send and receive information to software applications which use the barcode system.

Display 14 on device 12 presents an image associated with executable application 34 including a bar code. Communication processor 16 communicates a request for the bar code to a remote system (server 30). Communication processor 16 receives data representing the bar code for presentation in the image from the remote server system 30 in response to the request. The bar code is associated in at least one repository 17 of information, with a data destination associated with application 34 and particular bar code scanner 41 of multiple bar code scanners 26. Processor 16 receives data acquired using particular bar code scanner 41 for incorporation in the data destination in response to bar code scanning of an item with particular bar code scanner 41. Application 34 employs communication processor 16 in requesting from processor 30 unique bar codes associated with data destinations of application 34 and in receiving the barcode data.

System 10 uses barcode reader server 30 to send barcode data to a receiving system or device, such as device 12. An environment has n wireless barcode readers 26 which transmit their data to receiving server 30. Barcodes are generated and presented in an image provided by Application 34 (for example, on a patient header in a healthcare related system). The software generated onscreen barcodes are unique. When a user is ready to scan barcode data for a software application on a terminal or device, the user first scans the barcode on the screen of device 12. This unique barcode is recognized by barcode server 30 as representing a particular instance of a software application user interface image (by a specific session identifier of a webpage, by an identifier associated with the image or by another unique method of recognizing the specific image of images provided by multiple software applications). Data scanned by a barcode reader is transmitted to a software application 34 image to which the reader has been associated. Subsequently, if the image changes, the onscreen barcode is changed or is removed (and the association is discarded). In this case, system 10 requires a changed bar code to be rescanned to re-associate the barcode reader with application 34. A barcode which is scanned by the reader, while the reader is in an unassociated state, is ignored.

A healthcare or other hospital information system using Application 34 employing the barcode system uses a bidirectional interface with the barcode system for transmitting a unique one time barcode being used in an assigned location in an application image or workflow. In addition to transmitting the barcodes which are being displayed, Application 34 transmits to barcode server 30 a location ID (Session ID or other unique identifier) identifying where that unique barcode is being used. Application 34 has a receiving interface for receiving barcode data from the barcode server. This is data which starts with an association barcode and is followed by barcode data. When an association barcode is received by a receiving system, the subsequent associated barcode data is used in the context of the application workflow to which the association barcode belongs.

Figure 2:
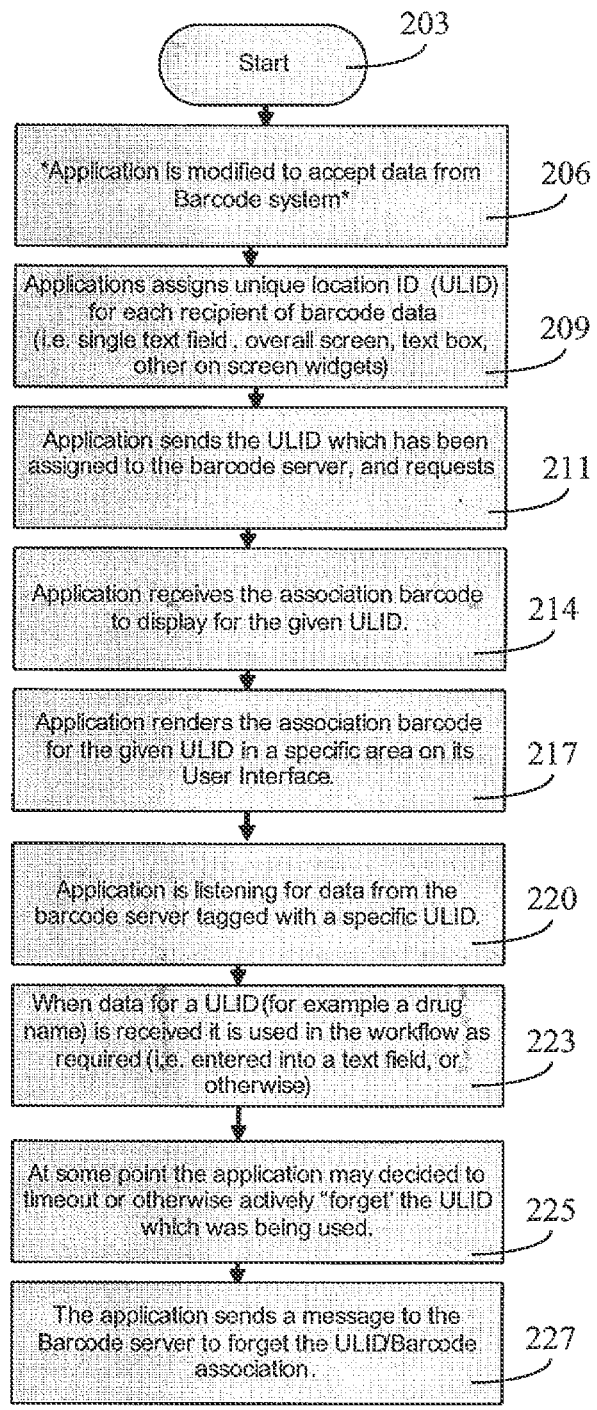
FIG. 2 shows a flowchart of a process for generating and processing bar code data, according to invention principles.

FIG. 2 shows a flowchart of a process for generating and processing bar code data. In one embodiment, following the start at step 203, Application 34 that is modified to acquire data from bar code processor 30 in step 206, employs lookup table 400 of FIG. 4 for associating a unique location, task or process type of associated executable Application 34 with a bar code scanner 41 acquired bar code data item. Table 400 of FIG. 4 shows a lookup Table linking a unique location identifier, task identifier or process identifier (ULID) (column 403) with unique location, task or process type (column 405) of an associated executable application and with a description (column 407). A unique location associated with an executable application may comprise, a displayed data field, text field, single display image, displayed button or displayed option list item or a memory location (not shown in Table 400), for example. A unique task associated with an executable application and having a task identifier, may comprise an individual workflow task performed by a user or processing device. A unique workflow process, or executable process associated with an executable application and having a process identifier, may comprise an individual workflow process performed by a user or processing device.

Figure 6:
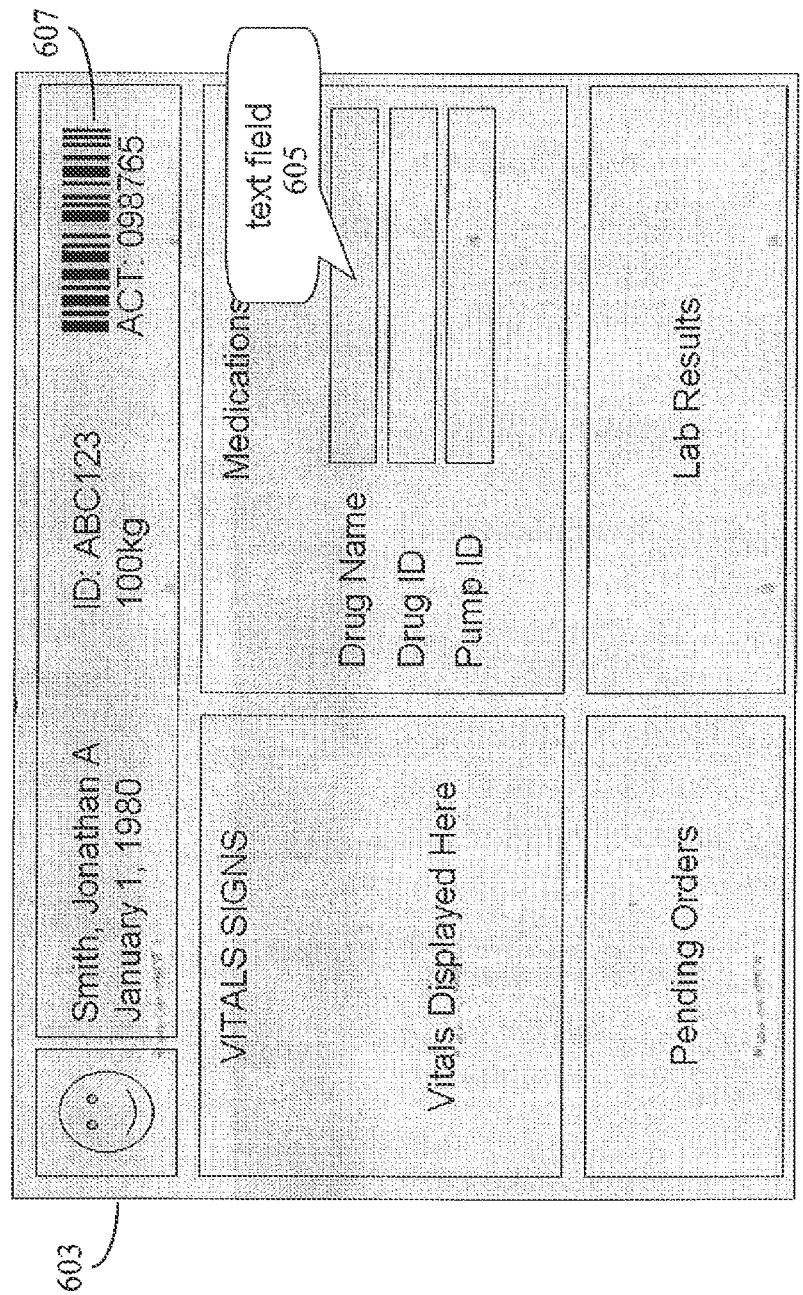
FIG. 6 shows a display image associated with a barcode for an application operation session and a barcode association with a particular text data field in the image, according to invention principles.

FIG. 6 shows display image 603 associated with barcode 607 presented in an Application 34 operation session and the system employs a barcode associated with particular text data field 605 in image 603. In one embodiment, image 603 uses a barcode for a whole computer operation or application operation session and in another embodiment uses a barcode associated with a particular text data field that is not associated with a complete operation session. Application 34 in step 209 (FIG. 2), employs lookup table 400 of FIG. 4 for associating a unique location, task or process type of associated executable Application 34 with a bar code scanner 41 acquired bar code data item. Specifically, Application 34 associates a unique location, drug name text data field 605 associated with executable Application 34 with a bar code scanner 41 acquired bar code data item. In step 211, Application 34 sends a particular unique location identifier (ULID) derived from Table 400 and assigned to text data field 605 to server 30 in a request for display of a bar code associated with data field 605. In step 214, Application 34 receives the requested bar code associated with data field 605 and in step 217 displays the bar code in data field 605 in image 603.

Figure 7:
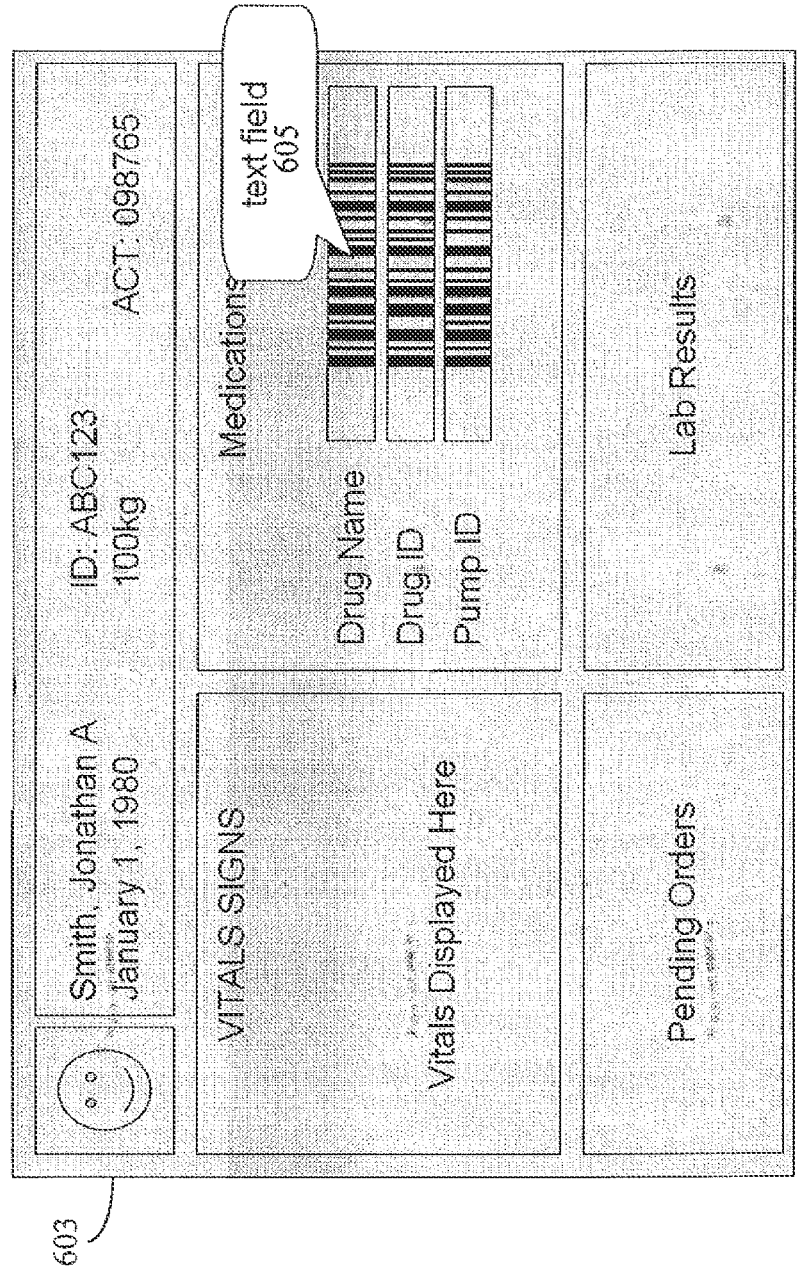
FIG. 7 shows a display image associated with a particular application having particular text data fields associated and populated with particular barcodes, according to invention principles.

Application 34 in step 220 listens for data from server 30 that is tagged with the particular ULID and in response to receiving data representing a drug name, for example, populates data field 605 of image 603 with the drug name in step 223 and uses the drug name in an associated drug administration workflow. In step 225, Application 34 after a predetermined timeout period actively discards the particular ULID being used and disassociates the particular ULID from data field 605. In step 227, Application 34 sends a message to server 30 to initiate discarding the association of the particular ULID with data field 605. The text data field 605 association is used and inactivated substantially when the data barcode is scanned and populated in text data field 605 as shown in FIG. 7. Specifically, FIG. 7 shows display image 603 associated with Application 34 having particular text data field 605 associated and populated with particular barcodes. The barcode system is also usable in embedded systems and in one embodiment a firmware upgrade enables use of the barcode system with a device in associated relevant workflows.

Figure 8:
FIG. 8 shows a display image associated with a particular application and infusion pump device having a bar code associated with a particular text data field and infusion pump data item, according to invention principles.
Figure 9:
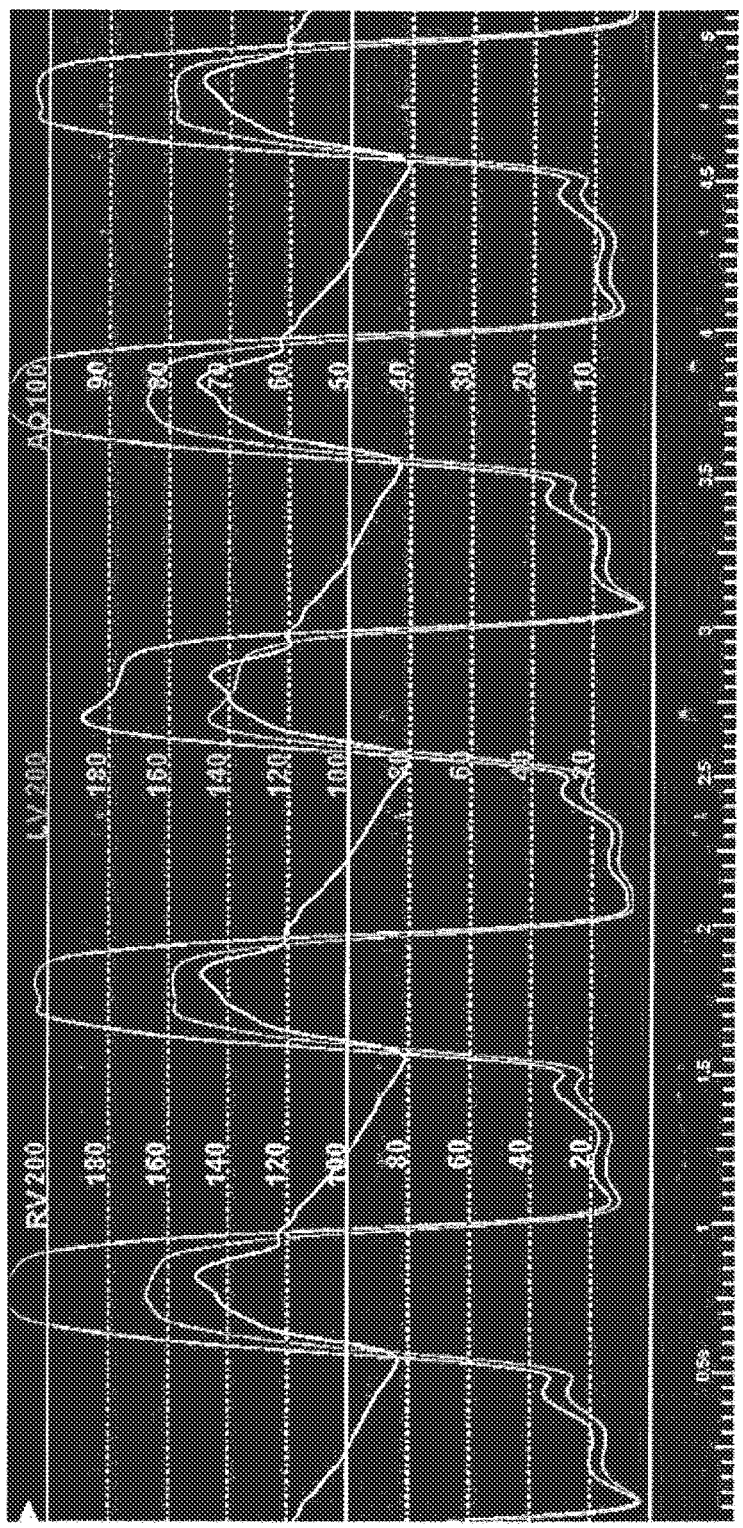
FIG. 9 shows a display of patient monitoring data of a particular patient associated with a patient monitoring device via a bar code association made using a bar code displayed in an image on the patient monitoring device, according to invention principles.

FIG. 8 shows display image 803 associated with a particular application and infusion pump device having a bar code 805 associated with particular text data field and infusion pump data item. In this example, the bar code system is used with an embedded device, an infusion pump. An infusion pump may employ firmware for controlling pump settings and other operational parameters of a device. The pump may also communicate with a pump server which monitors and communicates with multiple pumps. Modified pump firmware displays a barcode in an image on a pump display screen. The barcode is unique and generated by the system for one time use. A clinician, in response to connecting a pump to a patient scans the barcode on the image of the pump (the association barcode) presented on a pump display and scans the barcode on the wristband of the patient (the data barcode). Upon receiving both the association barcode and data barcode scans, the barcode server transmits to the pump gateway, information about the scan. The pump gateway is programmed to send the patient ID information to the pump and set that information in the pump memory. Future data from the pump is transmitted tagged with the correct patient identification information. FIG. 9 shows a display of patient monitoring data of a particular patient associated with a patient monitoring device via a bar code association made using a bar code displayed on an image on the patient monitoring device.

Figure 3:
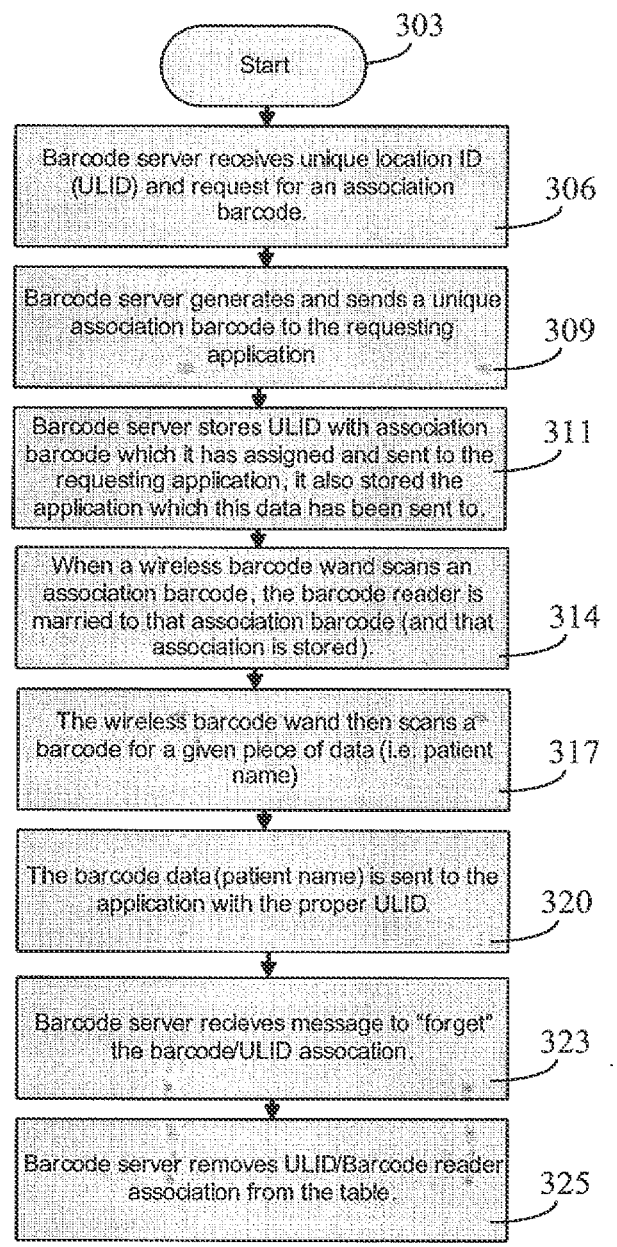
FIG. 3 shows a flowchart of a process for processing bar code data by a remote server, according to invention principles.

FIG. 3 shows a flowchart of a process for processing bar code data by remote processor (server) 30 (FIG. 1). In one embodiment, following the start at step 303, processor 30 interface 19 in step 306 receives a particular unique location identifier (ULID) from Application 34. In step 309, processor 30 generates a unique bar code or retrieves the unique bar code from storage and sends the unique bar code associated with the received ULID to Application 34 via interface 19. Processor 30 in step 311 stores the received ULID in table 500 of FIG. 5 in association with the generated or predetermined associated barcode. Table 5 (FIG. 5) links the received unique location identifier, task identifier or process identifier (ULID) (stored in column 503), with unique location, task or process type (column 505) of an associated executable application, the generated or predetermined associated bar code (column 507) sent to Application 34, bar code scanner identifier (column 509) and with an identifier of the executable application (Application 34, column 511).

In step 314, in response to scanner 41 scanning the unique bar code associated with the received ULID sent to Application 34 and displayed in text field 605 (FIG. 6), for example, scanner 41 is associated with the scanned unique bar code by storage of a scanner 41 identifier in Table 500. Scanner 41 is used in step 317, to scan an item of data e.g. a patient name in a wrist band bar code and in step 320 processor 30 sends the patient name to an Application (Application 34) associated with the ULID of the location associated with the unique bar code. In step 323, processor 30 receives a message commanding processor 30 to discard the association of the unique bar code and with the ULID. In one embodiment this message is generated in response to elapse of a timeout period, in another embodiment the message is generated in response to a command by Application 34. Processor 30 in step 325 updates Tables 400 and 500 to remove the association of the unique bar code with the ULID.

Figure 10:
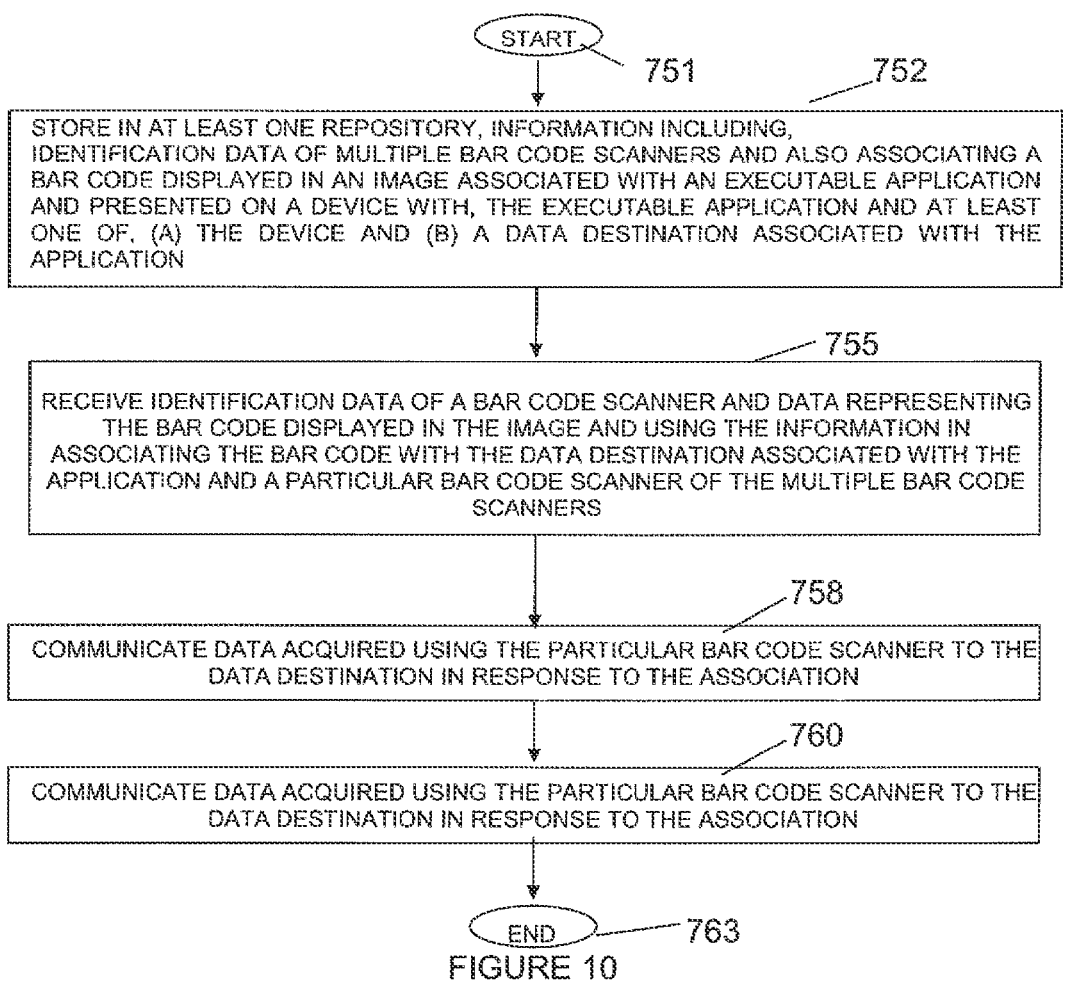
FIG. 10 shows a flowchart of a process employed by a bar code processing system, according to invention principles.

FIG. 10 shows a flowchart of a process employed by a bar code processing system e.g. processor 30 (FIG. 1) for processing bar code (e.g. bar code or a QR (quick response) code) data. Processor 30 in step 752 following the start at step 751, stores in at least one repository 17, information including, identification data of multiple bar code (e.g. wireless) scanners and also data associating a bar code displayed in an image associated with an executable application and presented on a device with, the executable application and at least one of, (a) the device and (b) a data destination (e.g. a data field in a displayed image) associated with the application. In one embodiment, the device is an infusion pump and processor 30 uses the information in associating the bar code with the infusion pump. In another embodiment, the device is an electronic device with a graphical user interface, and processor 30 uses the information in associating the bar code with the electronic device.

The information associates the bar code displayed in the image with elements including, at least one of, (a) a text field, (b) a workflow process, (c) a task identifier of a workflow process, (d) an image associated with the application, (e) a selectable button in the image associated with the application and (f) a value to be entered in an option list in the image associated with the application. Processor 30 uses the information in associating the bar code with at least one of the elements. In step 755, processor 30 receives identification data of a bar code scanner and data representing the bar code displayed in the image and uses the information in associating the bar code with the data destination associated with the application and a particular bar code scanner of the multiple bar code scanners. In one embodiment, a bar code scanner is a phone, computer or watch, for example.

Processor 30 in step 758, communicates data acquired using the particular bar code scanner to the data destination in response to the association. Processor 30, receives identification data of a first bar code scanner and data representing the bar code displayed in the image and identification data of a second bar code scanner and data representing the second bar code displayed in the image (or a second image). Processor 30 uses the information in associating the first bar code with a first data destination associated with the application and the first bar code scanner of the multiple bar code scanners and in associating the second bar code with a second data destination associated with the application and the second bar code scanner. Also processor 30 communicates data acquired using the first and second bar code scanners to the respective first and second data destinations in response to the association. In one embodiment, processor 30 dynamically generates the bar code displayed in the image and the bar code is acquired by the application. In step 760, processor 30 discards the association with the dynamically generated bar code displayed in response to completion of use of the bar code. Alternatively, processor 30 discards the association in response detection of completion of a workflow task. The process of FIG. 10 terminates at step 763.

Figure 11:
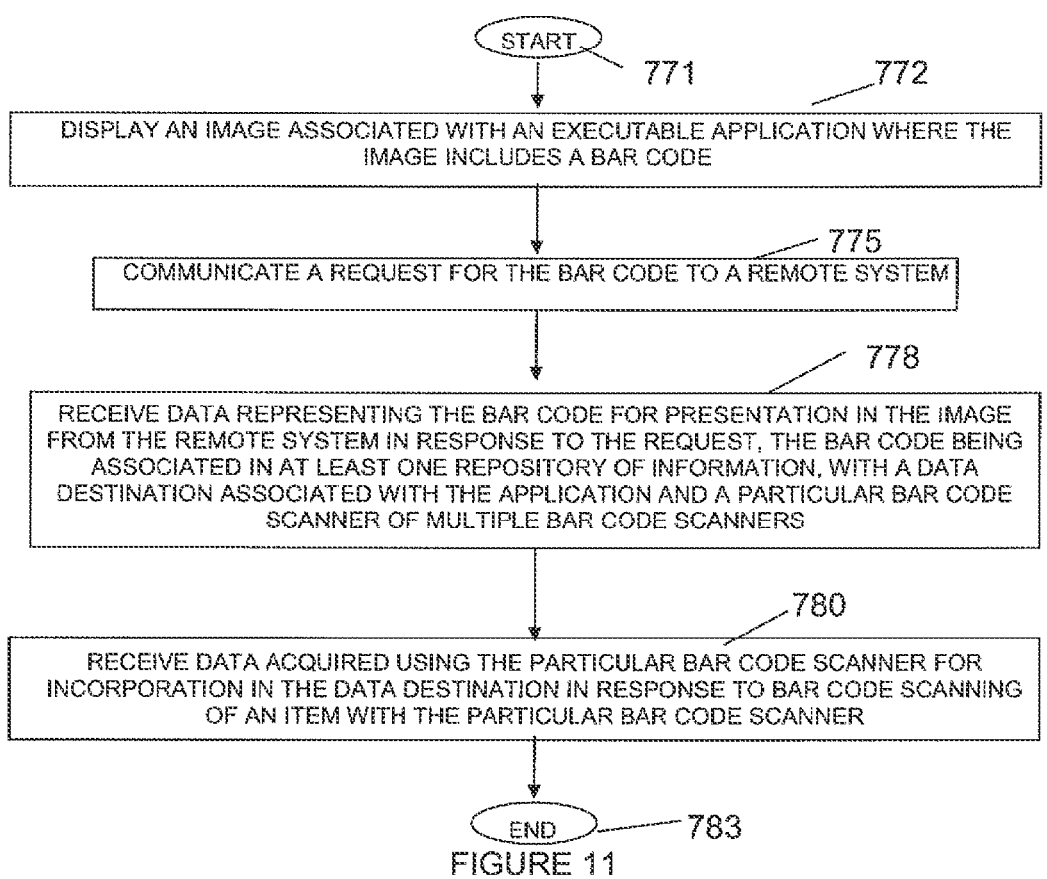
FIG. 11 shows a flowchart of a process employed by a bar code processing application, according to invention principles.

FIG. 11 shows a flowchart of a process employed by a bar code processing Application e.g. Application 34 (FIG. 1) for processing bar code data. Application 34 in step 772 following the start at step 711, displays an image associated with executable Application 34 and the image includes a bar code. In one embodiment, Application 34 operates on a computer in a medical device and the display resides on the medical device (e.g., an infusion pump). In step 775, Application 34 communicates a request for the bar code to a remote system (processor 30). In one embodiment Application 34 includes a communication processor and is within a computer provided on a mobile unit for use in patient rooms in a hospital. Application 34 in step 778, receives data representing the bar code for presentation in the image from the remote system in response to the request. The bar code is associated in at least one repository of information, with a data destination associated with the application and a particular bar code scanner of multiple bar code scanners. The at least one repository of information is within the computer or within the remote system. In step 780, Application 34 receives data acquired using the particular bar code scanner for incorporation in the data destination in response to bar code scanning of an item with the particular bar code scanner. The process of FIG. 11 terminates at step 783.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

Other Device Embodiments

Figure 12:
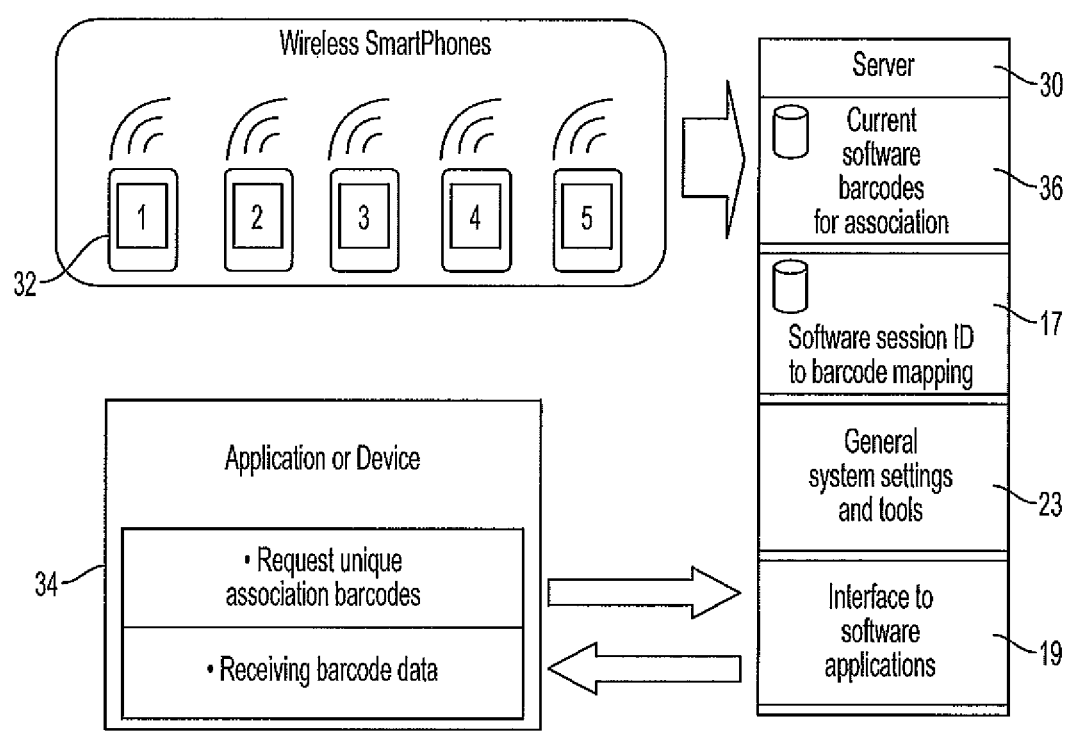
FIG. 12 shows a system for dynamically pairing devices with medical applications, according to one embodiment.
Figure 13:
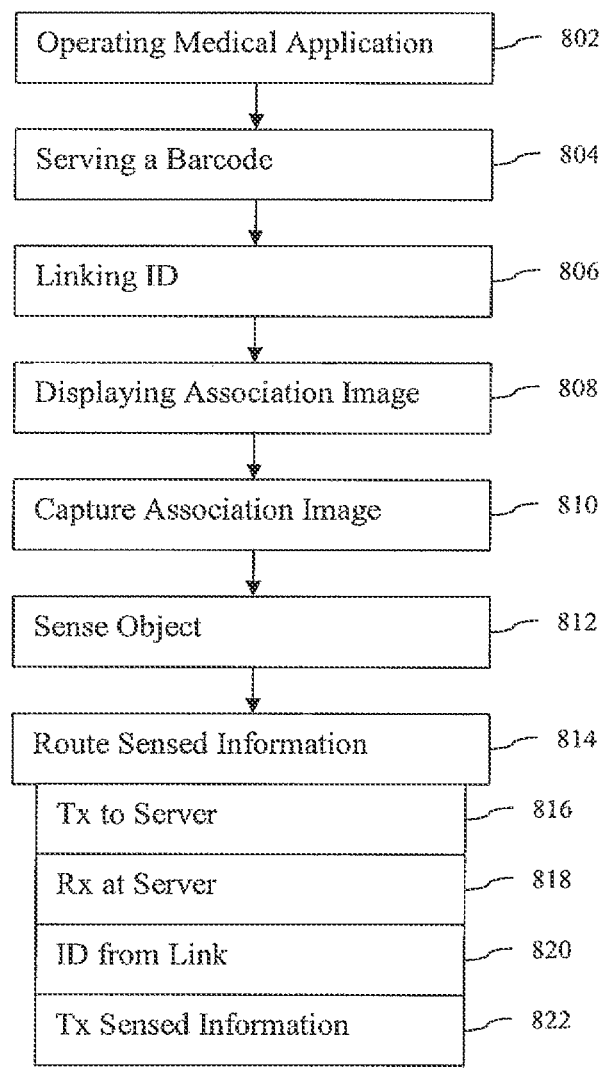
FIG. 13 shows a method for dynamically pairing devices with medical applications, according to one embodiment.

The systems and methods may be used for dynamic pairing of other devices than barcode readers with medical applications. FIGS. 12-13 show such embodiments. These embodiments use smart phones or other devices instead of the barcode readers, but may use barcode readers instead. While these other devices are not necessarily barcode readers, the method of association may still be via a barcode and/or barcode reading via a smartphone camera. The sensed data may be much more than just a barcode scan by using a smartphone or other non-barcode reader.

FIG. 12 shows one embodiment of a system for dynamic pairing of a device with a medical application (executable application). The system is the same or different than the system of FIG. 1, where the barcode readers are replaced with smart phones 32. Additional, different or fewer components may be provided. For example, other mobile or non-mobile devices are provided instead of one or more of the smart phones 32. As another example, an additional barcode server is provided for providing the barcode or related identifying information to the server 30 and/or the application 34. The system 12 implements the method of FIG. 13 or a different method.

The smart phone 32 sends an image or images from a camera to the appropriate receiving system, the application 34 or computer 12. The smart phones 32 communicate wirelessly with the server 30. Cellular, wifi, Bluetooth, or other wireless format is used. Any wired or wireless network is used for communications between the computer 34 and the server 30.

The server 30 is a barcode server or other server. The server 30 includes several modules 36, 17, 23, and 19. The repository 17 is a tracking module that tracks links between assigned barcodes and the computer 12 or application 34. The repository 17 is a look-up table or memory for mapping between currently associated smart phones 32 and live software sessions on the computer 12 and/or other computers. The system settings function 23 is a tool module that provides settings, configuration, or other tools to add (e.g., enable) smart phones 32 to be used in the system.

The interface 19 establishes communications in any format (e.g., TCP/IP) between the server 30 and the computer 12 or application 34. The interface 19 provides for two way communications. The unique one time barcode used in the assigned spot in the application screen/workflow may be transmitted from the server 30 to the computer 12, or identifying information may be transmitted from the application 34 on the computer 12 to the server 30. In addition to transmitting those barcodes or identifiers, the location ID (Session ID or other unique identifier) of the instance of the application is transmitted to the server 30. The server 30 associates the location or address of the application 34 on the computer 12 with the identifier to be displayed. More refined addressing may be used, such as indicating the text location of the application 34.

The server 30 receives identifying information and sensor data from the smart phones 32. For example, image data captured by the smart phone 32 and identifying information also captured by the smart phone 32 from the display 14 is received by the server 30. The server 30 determines the destination address for the image data using the repository 17, and forwards the image data to the application.

For the application 34 on the computer 12, the display 14 is configured by software and/or hardware to present an image associated with an executable electronic medical record application or other medical application of the computer 12. The image includes identifying information, such as a barcode, QR code, other code, text with patient identification, other image of the patient's electronic medical record, or other unique identifier of the instance of the application being run. The identifying information is unique as compared to other instances of the application that may be running on the same or other computers 34. The identifying information is either part of the patient medical record or other application or is queried for and received from the server 30 or another server.

The processor 16 is the communication processor or other processor. The processor 16 is configured by software and/or hardware to communicate with the server 30 about the identity information. For example, a barcode is requested and received by the processor 16. As another example, the processor 16 transmits identification information (e.g., a patient number, a screen shot, or both) for an instance of the application to the server 30. The identification information from the processor 16 may be used by the server 30 for matching with a picture or other data captured by the smart phone 32 on the display 14.

The processor 16 is configured to receive sensor data from the remote server 30. The sensor data is any data sensed by the smart phone 32. The sensor data is different from the captured identification information, such as being a picture of the patient. The smart phone 32 also senses the identification information (e.g., picture of displayed barcode) on the display 14. The identification information captured by the smart phone 32 is used to route the sensor data to the application 34 on the computer 12, and is or is not also provided to the application 34. The received sensor data is inserted into a patient's electronic medical record of the executable electronic medical record application or otherwise used by the medical application. For example, the sensor data (e.g., picture of the patient) is displayed in the patient's electronic medical record at the computer 34.

The smart phone 32 is a cellular phone, such as a personal phone. Multiple smart phones 32, such as for different users of a medical network, are available for use in sensing information for different instances of the application. At a given time, a smart phone 32 may be linked to a given instance of the medical application by the identifying information on the display 14 captured by the smart phone. The smart phone 32 includes a processor operable to run a relation application for communicating sensed data and identifying information (e.g., an image output on the display 14 or a code extracted from such an image) to the server 30.

One, more, or all of the smart phones 32 may be replaced with other devices. For example, personal data assistants, laptops, tablet computers, or other mobile devices may be used. As another example, embedded devices (e.g., EKG, PulseOx, or other medical devices) may include a display 14 of identifying information. Embedded systems may have no option of taking advantage of barcode readers due to hardware limitations. Ancillary sensor hardware, such as the scanner or sensor for sensing identification from the display, may be used here to overcome such hardware limitations. This technology may be used with the embedded devices in their relevant workflows.

The smart phone or other device to be dynamically linked includes one or more sensors. At least one of the sensors captures or reads the display 14. The same or a different sensor measures a characteristic of a patient, prescription bottle, medical order, or other medical related object. For example, the camera of the smart phone may be used for both detecting the identifying information for the medical application and sensing an object. Infrared (e.g., barcode scanner), temperature, pressure, humidity, ultraviolet, radiation, or other types of sensors may be provided on the device or connectable with the device. Any property may be sensed, such as sound, smell or temperature.

The computer running the medical application 34 also includes a memory. Another memory is provided for the server 30. Yet another memory is provided on the smart phone 32. The memories are non-transitory computer readable storage medium having stored therein data representing instructions executable by a programmed processor for dynamic pairing of a device with a medical application. For example, the processor 16 operates pursuant to instructions. The instructions and/or transaction data are stored in a non-transitory computer readable memory such as an external storage, ROM, and/or RAM. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

FIG. 13 shows one embodiment of a method for dynamic pairing of a mobile device with a medical application. The method is performed by the system of FIG. 1 or 12, or a different system. Additional, different, or fewer acts may be provided. For example, acts performed just from the perspective of the sensor device (e.g., smart phone), of the server, or of the application are performed. As another example, act 804 is not performed, such as where the unique identification information originates from the medical application. The acts are performed in the order shown or a different order.

In act 802, a medical application is operated on a computer. The computer is part of an enterprise network, such as part of a hospital network.

Figure 14:
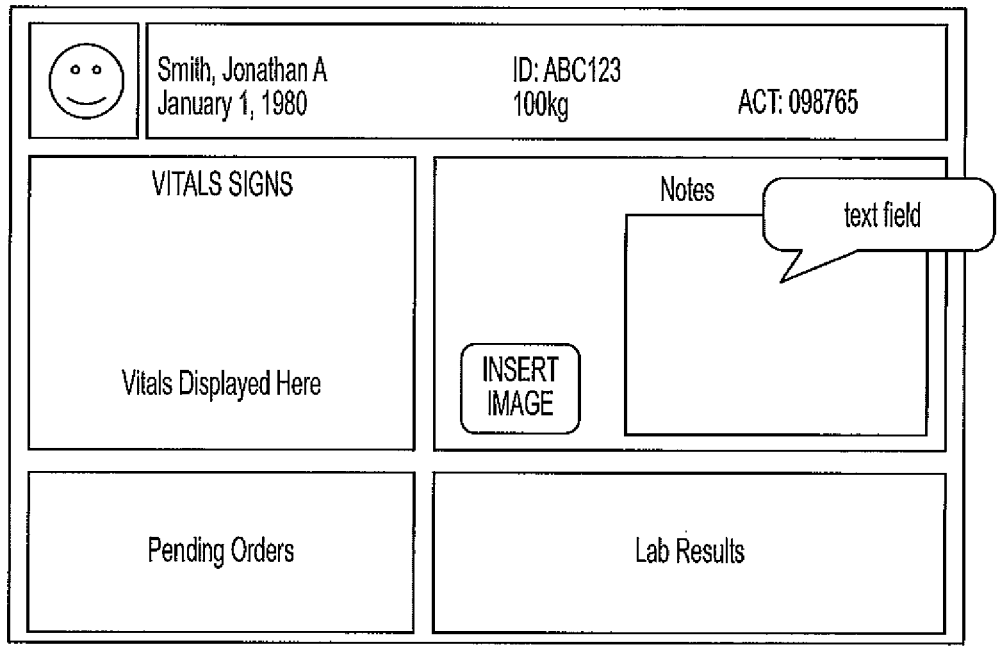
FIG. 14 shows an example display image of a medical record application where the display image includes a user interface option to add an image.

The medical application is a workflow, electronic medical record, radiology, laboratory, pharmacy, or other medical application. In one embodiment, the medical application is an electronic medical record application for providing access to and storing patient information. The medical application may be operated on one or more computers. For operation on a given computer, the medical application may be configured to present a user interface for a particular patient. FIG. 14 shows one example. Any user interface may be used. Other instances of the medical application on the same or different computers may present medical records for other patients. Each instance may access stored patient information from a database over the network. For networked operation, each instance is assigned a port, session identifier, address, or other designator for communicating in the network with the instance and not other instances.

The medical application includes one or more options for inputting information. For example, FIG. 14 shows the options to input text and an image. Other inputs may be provided. The inputs allow updating information, adding information, or creating a document. A user may add a note, upload an image for analysis, or record a current condition using the medical application. For example, the user opens the electronic medical record for Jonathan A. Smith and wants to add an image associated with text notes also being added. A button or other input option allows the user to select addition of the image. The user activates the input option (e.g., presses an insert photo button on the report/note application toolbar on the electronic medical record).

In act 804, a bar code is served to the computer from a remote server, such as a server for communications or a separate barcode server. The barcode is generated as being unique within a time period or different than other barcodes created for the network. The medical application requests the barcode for dynamically linking a smart phone. In response, the barcode server provides a bar code.

The barcode is provided in response to the user selecting entry of sensor data from the smart phone. Alternatively, the medical application is assigned or pre-requests one or more barcodes for later use.

In alternative embodiments, the medical application includes unique identification information for a given instance without requesting from another source. For example, a picture of the overall layout of the display, the displayed patient name, a displayed patient identifier, and/or a randomly generated displayed identifier based on possibly unique information is provided. For these resident identifiers, the medical application communicates the identifier to the communications server for routing sensed data from the "to be linked" smart phone.

In act 806, the identifier is linked with an instance of the medical application 34 running on the computer. The linking occurs at the server. A map relating the address or other communication information for the instance with the identifier is created. This association allows the server to use the identifying information to determine where to send sensed data. For example, a bar code image or a code extracted from the barcode image is stored in a table with a session ID for the instance of the application.

To link, the server provides or receives the identifier or information extracted from the identifier in communications with the instance of the medical application. The communications are used to extract or parse the session ID, address, or other communications information unique to the instance of the medical application. For example, the server transmits the barcode to be used to the instance in response to a request for the barcode from the instance. As another example, the server receives identifying information, such as a picture of a face of the patent and/or a patient identity number in communications, so links this identifier with the instance.

In act 808, the computer running the application displays an association output image on the display. The association output image is an image that includes the identifying information to be used to dynamically link the smart phone to the instance of the application or to the computer running the instance.

The display of the identifying information in an image occurs in response to user activation in the medical application. The user selects an option to add data. In response, the medical application obtains the identifying information and displays the identifying information or information created from the identifying information for capture by the smart phone. Alternatively, a workflow or other medical application may display the association output image as part of progression in the workflow or in response to another trigger. In yet other embodiments, an already occurring display may be used as the association output image without triggering a specific display.

Figure 15:
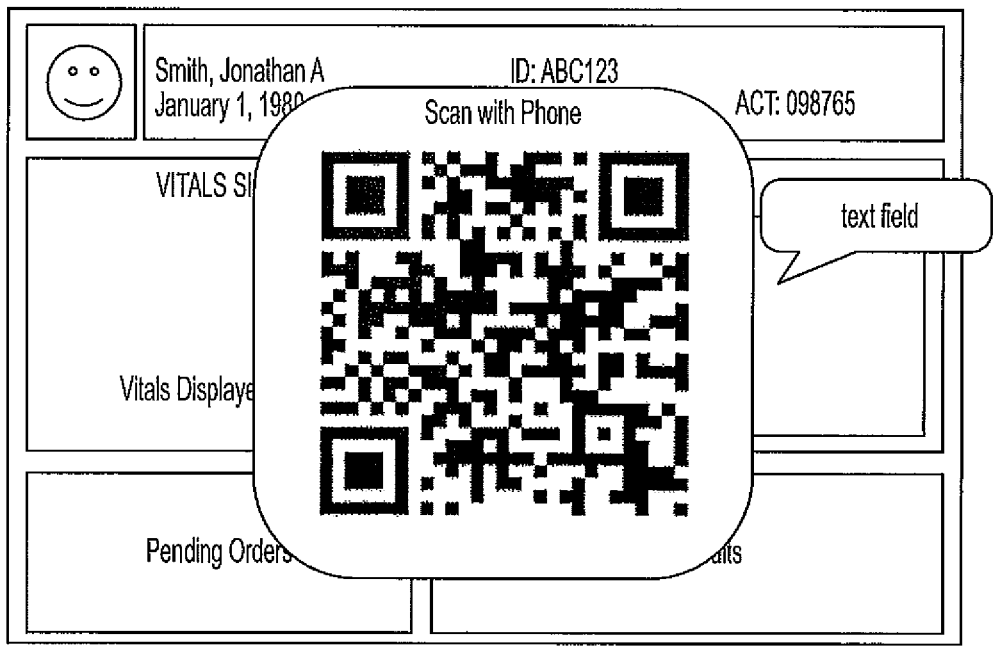
FIG. 15 shows an example display image of a QR code displayed by a medical record application.

FIG. 15 shows an example display of a QR code obtained from the server. The instance of the medical application causes the QR code to be displayed in response to the user selecting a button. The QR code is the association output image. The face of the patient and/or the patient identifier may be used instead or in addition.

The identifying information in the association output image is to be used to link the smart phone to the computer or instance of the medical application at the time of the displaying. Thus, the link is dynamic since it may change or occurs as needed.

FIG. 15 is a screenshot representing how the system takes advantage of a QR code association for a particular purpose on a screen. When the workflow is ready for the image, a QR code is drawn by the software application on a specific screen. The insert image button, upon being pressed, generates a QR code which is then to be scanned with a smart phone. The barcode is displayed as an overlay or dominant portion of the image or may be smaller or larger (e.g., on the patient header in the medical application). These software generated onscreen QR codes are unique. The association image (e.g., QR code) stays on the screen until the association is used and is removed as soon as the image data has been acquired into the system or after a timer expires.

In act 810, the association output image is captured. The smart phone or other device images the image on the display of the computer. Any sensing may be used to capture, such as using a camera to take a picture of the image. As another example, a barcode reader scans the image. When a user is ready to insert the image or other sensed data into the medical application, the user scans the barcode on the screen, such as with the camera on the smart phone.

The smart phone may include an application. The user launches the application. In response, the user is prompted to capture the displayed identifying information. Alternatively, the association output image includes a trigger or coding that causes the application to launch when the image is captured. In yet other alternative embodiments, an application is not provided on the smart phone. The user is informed or trained of a communications address to send the captured identity information and sensed data via e-mail, text, or other modality.

In act 812, an object property is sensed. The smart phone is used to sense an object, such as capturing a picture of a patient. Any medical related object may be sensed. Any type of sensing may be used. The sensing acquires data to be used by the medical application. For example, a picture of a wound is taken using the camera on the smart phone. Other properties associated with the patient may be sensed, such as temperature, sound, or smell.

The user is prompted to sense the object by instructions on the display of the computer, a display on the smart phone, or knowledge. After, during, or before capture of the identifying information from the display, the smart phone is used to sense data to be provided to the medical application.

In act 814, the sensed information is routed to the computer and instance of the medical application. The routing uses the captured association output image. Upon image acquisition on the smart phone, the image or other sensed data is sent and imported into the note which was being typed on the current session on the medical application. The route is from the smart phone, to the server, and then to the instance of the medical application. Acts 816, 818, 820, and 822 represent acts performed as part of this routing. Additional, different, or fewer acts may be performed for routing.

In act 816, the smart phone communicates with the server. Using the application or known address, the smart phone transmits the sensed information and identifying information to the server. The identifying information is as captured or derived from the captured display. For example, the captured image is sent. As another example, the smart phone application processes the captured output association image to extract a code or other identifying information. The extracted identifying information is sent to the server.

Upon transmission, the smart phone automatically deletes the sensed information from the smart phone. This avoids any unintentional storage of sensitive medical information about a patient. Similarly, the association output image or indentifying information extracted from the image may be removed from the smart phone. This data is deleted once the transmission occurs. The association between the identifying information and the sensed data may alternatively or additionally be deleted. In other embodiments, the sensed data and identifying information are maintained until an acknowledgement of receipt is received from the server, until manually deleted, or until another triggering event.

In act 818, the server receives the sensor data and the identifying information from the smart phone. The identifier as captured or the identifier extracted from the captured association output image is received along with the sensed data. For example, a code extracted from a barcode displayed by the medical application is received with an image of the patient. As another example, the picture of the association output image displayed by the medical application is received with an image of the patient.

The sensed data and identifier are received in a message using any communications. E-mail, text, TCP/IP, or other communications format is used. The sensed data and identifier are received as one package or one stream. Alternatively, the sensed data is received separately from the identifier, but the smart phone address or other identifier and other code links the different data together.

In act 820, the instance of the medical application or computer running the instance is identified. The identifying information received from the smart phone is known to the server. By comparing the received identifying information with a table of identifying information, the communications information for the instance or computer is located.

Where the captured association output image is received, the server may extract a code or other identifying information for looking up the communications information. Any image processing may be used. For example, correlation is performed to determine a sufficient match of images. As another example, a numeric or alphanumeric code is extracted from the image and the code is used for the look-up. Facial pattern recognition may be used. Alternatively, the code extracted by the smart phone is received and used for looking up without further processing.

The identifying information is used to associate the sensed data with the instance of the medical application running on the remote computer. To complete the routing, the computer or the instance is identified. The link created in act 806 is used to determine where to send the sensed data. For example, the unique barcode is recognized by the server as representing a particular instance of a software application screen (e.g., as being for a specific session ID of a webpage or some other method of recognizing that specific screen within the network of software applications).

In an alternative or additional embodiment, the patient is identified. Identifying the patient may allow routing to a database or other storage of information associated with the instance of the medical application. Rather than or in addition to updating the medical application on the computer, the sensed data is provided to a database or other networked location for storing information for that patient or medical application.

Figure 16:
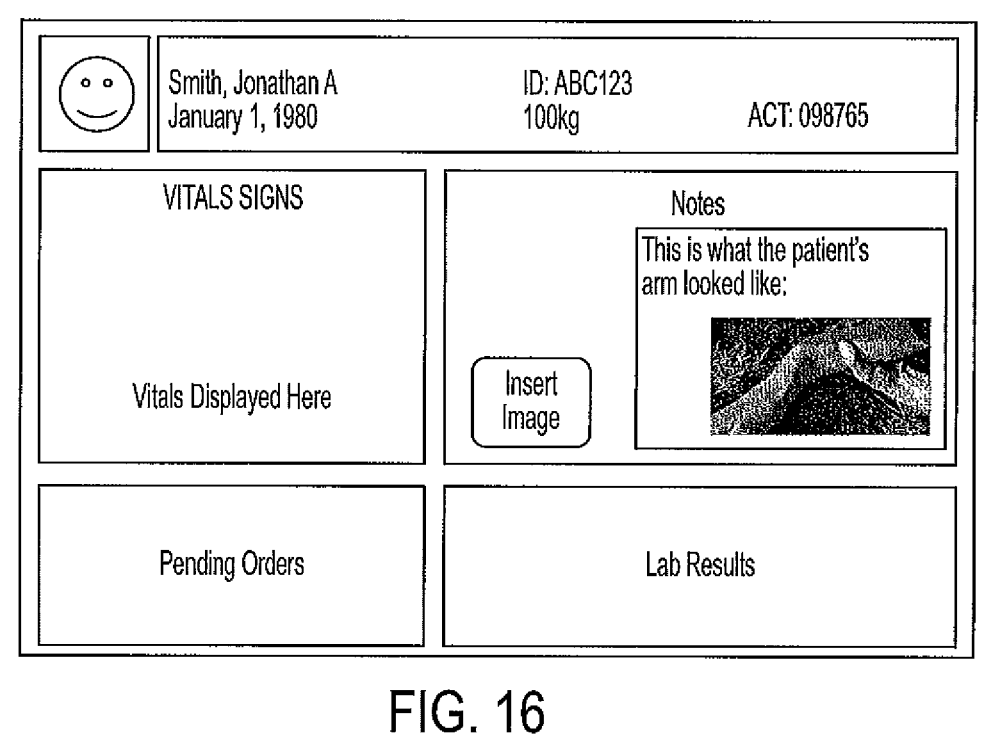

In act 822, the sensed information from the smart phone is transmitted by the server to the computer, to the instance of the medical application operating on the computer, to a database of the patient medical record of the patient, or combinations thereof. The identified communications address (e.g., session ID) is used to determine where to send the sensed information. The server outputs the sensed information to the located instance, computer, or database. For example, the image captured by the smart phone camera is transmitted to the software application screen to which the smart phone has been associated. FIG. 16 shows the instance of the medical application on the computer having been updated with the image from the smart phone. Text is also added by the user. The text describing the sensed data may be added at the smart phone or at the user interface of the computer.

The update occurs locally or at the computer. The update may alternatively or additionally be propagated to a database or other networked host for the medical application. For example, the electronic medical record of the patient is updated with the sensor data at a database. This update is performed by the instance, which also updates the display.

The same smart phone may be later linked to the same or different computer or instance of the medical application. For example, another dynamic pairing is created for acquiring further sensed data for a patient. As another example, the user of the smart phone travels to another room with a different patient. A computer in this other room has a different instance of the medical application for this different patient. The same smart phone is now linked to this different instance for updating the medical record or other application related to this different patient. The acts (e.g., operating, displaying, capturing, sensing, and routing) are repeated throughout a facility or medical institution with any number of instances and smart phones. The repetition may occur for the same patient to add information to another part of the medical record, such as adding an image for skin conditions section and adding a different image for a general section of the patient's medical record.

The system and processes of FIGS. 1-16 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system associates barcodes which may include both physical barcodes and dynamically created on-screen software generated barcodes with a software application, image, memory location, data field, process, workflow, or text field allowing greater flexibility than associating a bar code reader to a complete device. Further, the processes and applications may, in alternative embodiments, be located on one or more (e.g., distributed) processing devices on a network linking the units of FIG. 1 or 12. Any of the functions and steps provided in FIGS. 1-16 may be implemented in hardware, software or a combination of both.

What is claimed is:
1. A method for dynamic pairing of a mobile device with a medical application, the method comprising:
operating the medical application on a computer, the medical application including patient information from a patient medical record of a patient;
displaying an association output image on a display of the computer, the association output image linked to the medical application on the computer;
capturing the association output image on the display with the mobile device;

acquiring a medical image associated with the patient with the mobile device; and routing the medical image from the mobile device to the medical application on the computer using the captured association output image.

2. The method of claim 1 wherein operating comprises operating an electronic medical record application.

3. The method of claim 1 wherein displaying comprises displaying a bar code obtained from a server, the bar code linked to the patient medical record operating on the computer at the time of the displaying.

4. The method of claim 1 wherein displaying comprises displaying the patient medical record as the association output image;

further comprising:

identifying the patient medical record from the displayed patient medical record.

5. The method of claim 1 wherein displaying comprises displaying in response to user activation of an input option in the medical application.

6. The method of claim 1 wherein capturing comprises capturing with a camera of the mobile device.

7. The method of claim 1 wherein acquiring a medical image comprises taking a picture of the patient with the mobile device.

8. The method of claim 1 wherein the mobile device is a smart phone having an application for capturing images and wherein the application communicates the medical image with the association output image or with information derived from the association output image.

9. The method of claim 1 wherein routing comprises transmitting the medical image and the association output image or information derived from the association output image to a server, the server identifying an instance of the medical application operating on the computer from the association output image or information derived from the association output image and transmitting the medical image to the computer, to the instance of the medical application operating on the computer, to a database of the patient medical record of the patient, or combinations thereof.

10. The method of claim 1 further comprising:

serving a unique bar code to the computer from a server;

linking the unique bar code to an instance of the medical application running on the computer; and identifying the medical application or computer from a message received from the mobile device containing the sensing information and association output image.

11. The method of claim 1 further comprising:

repeating the operating, displaying, capturing, acquiring, and routing with the mobile device and a different computer, different patient medical record, different part of the patient medical record, and different patient.

12. The method of claim 1 further comprising automatically deleting the medical image from the mobile device after transmitting the medical image from the mobile device.

13. The method of claim 1, wherein acquiring a medical image comprises scanning a barcode on a medical related object.

14. A non-transitory computer readable storage medium having stored therein data representing instructions executable by a programmed processor for dynamic pairing of a device with a medical application, the storage medium comprising instructions for:

linking an identifier to an instance of a medical application running on a remote computer;

receiving a medical image and the identifier from the device, the identifier displayed by the remote computer and captured by the device from the display;

associating, with the identifier, the medical image with the instance of the medical application running on the remote computer; and outputting the medical image to the instance of the medical application running on the remote computer.

15. The non-transitory computer readable storage medium of claim 14, wherein linking comprises transmitting a barcode to the instance of the medical application in response to a request for the barcode from the instance of the medical application, wherein receiving comprises receiving a code of the barcode from the device after the device captures the barcode on the display, and wherein outputting comprises updating an electronic medical record of a patient with the medical image.

16. The non-transitory computer readable storage medium of claim 14, wherein receiving the medical image comprises receiving an image of a medical object captured by the device, the device comprising a smart phone.

17. The non-transitory computer readable storage medium of claim 14, further comprising:

automatically removing the association of the identifier with the instance of the medical application after the medical image has been received by the medical application.

18. A system for dynamic pairing of a device with a medical application, the system comprising:

a display on a computer, the display configured to present an image associated with an executable electronic medical record application of the computer; and a processor of the computer, the processor configured to communicate identity information for the image with a remote server, to receive sensor data from the remote server, the sensor data and the image sensed by the device, and to insert the sensor data into a patient's electronic medical record of the executable electronic medical record application.

19. The system of claim 18 wherein the display is configured to present the image as a bar code, wherein the bar code is generated as being unique within a time period or different than other bar codes creates for the network, wherein the processor is configured to receive the barcode as the identity information from the remote server, wherein the processor is configured to receive the sensor data as a picture captured by the device, the device comprising a smart phone, the smart phone capturing the barcode on the display, and wherein the processor is configured to display the patient's electronic medical record with the sensor data.

20. The system of claim 18 wherein the image comprises an image of the patient's electronic medical record, and wherein the processor is configured to transmit the image or information about the image to the remote server for comparison of a picture captured by the device with the image or the information.

* * * * *